(12) United States Patent
Morris et al.

(10) Patent No.: US 11,180,508 B2
(45) Date of Patent: Nov. 23, 2021

(54) CHEMICAL PROCESS FOR THE SYNTHESIS OF HERBICIDAL PYRAZOLIDINEDIONE COMPOUNDS

(71) Applicant: Syngenta Participations AG, Basel (CH)

(72) Inventors: James Alan Morris, Bracknell (GB); Alexandr Shafir, El Vendrell (ES); Mallikharjuna Gonu, Ilhas Goa (IN); Iffat Bilal, Ilhas Goa (IN); David Alexander Sale, Bracknell (GB)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/770,377

(22) PCT Filed: Dec. 4, 2018

(86) PCT No.: PCT/EP2018/083544
§ 371 (c)(1),
(2) Date: Jun. 5, 2020

(87) PCT Pub. No.: WO2019/110613
PCT Pub. Date: Jun. 13, 2019

(65) Prior Publication Data
US 2021/0171540 A1    Jun. 10, 2021

(30) Foreign Application Priority Data

Dec. 5, 2017 (IN) .............................. 201711043641

(51) Int. Cl.
C07D 498/04    (2006.01)
B01J 31/24     (2006.01)
B01J 31/28     (2006.01)

(52) U.S. Cl.
CPC ............ *C07D 498/04* (2013.01); *B01J 31/24* (2013.01); *B01J 31/28* (2013.01)

(58) Field of Classification Search
None
See application file for complete search history.

(56) References Cited

U.S. PATENT DOCUMENTS

2005/0187110 A1   8/2005   Maetzke et al.
2012/0190865 A1   7/2012   Fischer et al.

FOREIGN PATENT DOCUMENTS

WO    0078881 A2   12/2000
WO    0117973 A2    3/2001

OTHER PUBLICATIONS

Written Opinion and International Search Report for PCT/EP2018/083544, dated Jan. 23, 2019.
Muelebach et al., Pest Management Science 2011, 67, 1499-1521, XP055539325.
Storgaard et al., J Org Chem 2009, 74, 5032-5010, XP007918205, cited in application.
McGarry et al., Polyhedron 2015, 114, 101-109, XP029599915.

*Primary Examiner* — Joseph R Kosack
(74) *Attorney, Agent, or Firm* — BakerHostetler; Toni-Junell Herbert

(57) ABSTRACT

The present invention relates to a novel process for the synthesis of herbicidal pyrazolidinedione compounds. In particular, a process for the preparation of a compound of formula (I), wherein $R^1$, $R^2$ and $R^3$ are as defined herein. The present invention further relates to novel intermediate compounds utilized in said process, and methods for preparing said intermediate compounds.

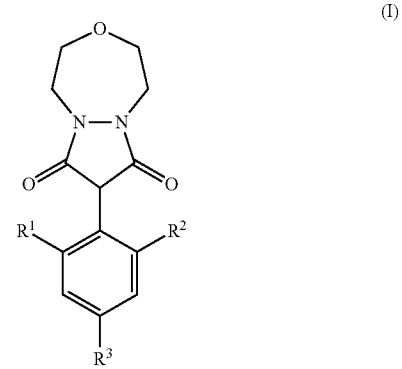

(I)

15 Claims, No Drawings

CHEMICAL PROCESS FOR THE SYNTHESIS OF HERBICIDAL PYRAZOLIDINEDIONE COMPOUNDS

CROSS-REFERENCE TO RELATED APPLICATIONS

This application is a 371 National Stage application of International. Application No. PCT/EP2018/083544 filed Dec. 4, 2018 which claims priority to IN 201711043641, filed Dec. 5, 2017, the entire contents of which applications are hereby incorporated by reference.

The present invention relates to a novel process for the synthesis of herbicidal pyrazolidinedione compounds. Such compounds are known, for example, from WO 01/17973 and processes for making such compounds or intermediates thereof are also known, for example, from WO 00/78881 or WO 2004/050607. Such compounds are typically produced from the condensation reaction of [1,4,5]oxadiazepene (or salt thereof) and a di-ortho alkyl substituted phenylmalonic acid diamide.

However, there exists the need for a more convergent route to the synthesis of such compounds that is more cost effective and that reduces the number of steps required. Furthermore it would be beneficial for a process to avoid the generation of certain undesirable by-products.

The coupling of di-ortho substituted aryl-lead reagents with cyclic 1, 3-diones is known (see for example WO 2012/165648), however, such a process has a number of drawbacks. Firstly, this approach requires the synthesis of the organolead species, which can be time-consuming and involve the use of catalytic quantities of toxic Hg(II) and secondly, a by-product of this reaction is stoichiometric quantities of $Pb(OAc)_2$.

Palladium catalysed α-arylation of cyclic 1, 3-diones are known as a quicker and safer method, for example, *J. Am. Chem. Soc.* 2000, 122, 1360-1370, but examples of palladium catalysed coupling of di-ortho substituted aryl halides or pseudo halides are not reported. Ortho-substituted aryl halides are known to be challenging substrates for such a reaction, see *J. Org. Chem.* 2009, 74, 5032-5040.

Mono ortho-substituted aryl halides have been shown to undergo the desired transformation with $Pd(OAc)_2$ as a catalyst (see US2012/0190865), however, it has been shown that this catalyst is not suitable for reactions of the present invention.

Surprisingly, we have now found that such an α-arylation process can be achieved on a di-ortho substituted aryl halide or pseudo halide when certain defined palladium catalyst are employed. Such a process is more convergent, which may be more cost effective and may produce less waste products.

Thus, according to the present invention there is provided a process for preparation of a compound of formula (I)

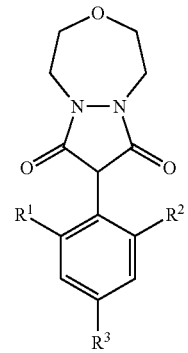

wherein
each $R^1$ and $R^2$ are independently $C_1$-$C_4$alkyl;
$R^3$ is selected from the group consisting of hydrogen and $C_1$-$C_4$alkyl;
said process comprising reacting a compound of formula (II)

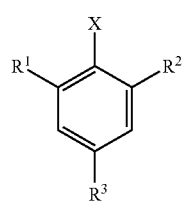

wherein
X is selected from the group consisting of Br, Cl, $CF_3SO_3$—, $CH_3C_6H_4SO_3$— and $CH_3SO_3$—, and $R^1$, $R^2$ and $R^3$ are as defined herein, with a compound of formula (III)

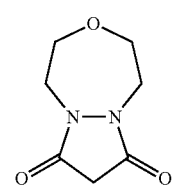

the reaction being carried out
in the presence of a π-allylpalladium complex; and a phosphine ligand of the formula (IV)

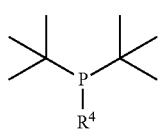

or a suitable salt thereof,
wherein
$R^4$ is selected from the group consisting of $C_1$-$C_6$alkyl, $C_5$-$C_6$cycloalkyl, phenyl and heteroaryl, wherein the heteroaryl is a 5- or 6-membered aromatic ring which comprises 1 or 2 heteroatoms independently selected from N and O, and wherein the phenyl or heteroaryl are optionally substituted by 1, 2, 3, 4 or 5 $R^5$ substituents, which may be the same or different;

$R^5$ is selected from the group consisting of halogen, $C_1$-$C_4$alkyl, $C_1$-$C_4$alkoxy, N—$C_1$-$C_4$alkylamino, N,N-di$C_1$-$C_4$alkylamino and phenyl, wherein said phenyl is optionally substituted by 1, 2, 3 or 4 $R^6$ substituents, which may be the same or different;

$R^6$ is selected from the group consisting of $C_1$-$C_4$alkyl, $C_1$-$C_4$alkoxy, N—$C_1$-$C_4$alkylamino and N,N-di$C_1$-$C_4$alkylamino;

and a base.

According to a second aspect of the invention, there is further provided an intermediate compound of formula (III):

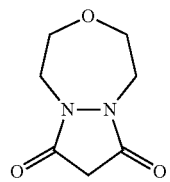

(III)

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. $C_1$-$C_4$alkyl and $C_1$-$C_2$alkyl are to be construed accordingly. Examples of $C_1$-$C_6$alkyl include, but are not limited to, methyl, ethyl, n-propyl, 1-methylethyl(iso-propyl), n-butyl, and 1-dimethylethyl(t-butyl).

As used herein, the term "$C_1$-$C_4$alkoxy" refers to a radical of the formula —$OR_a$ where $R_a$ is a $C_1$-$C_6$alkyl radical as generally defined above. Examples of $C_1$-$C_4$alkoxy include, but are not limited to, methoxy, ethoxy, propoxy, iso-propoxy and t-butoxy.

As used herein, the term "N—$C_1$-$C_4$alkylamino" refers to a radical of the formula —$NHR_a$ where $R_a$ is a $C_1$-$C_4$alkyl radical as generally defined above.

As used herein, the term "N,N-di$C_1$-$C_4$alkylamino" refers to a radical of the formula —$N(R_a)R_a$ where each $R_a$ independently of each other is a $C_1$-$C_4$alkyl radical as generally defined above.

As used herein, the term "$C_5$-$C_6$cycloalkyl" refers to a stable, monocyclic ring radical which is saturated or partially unsaturated and contains 5 to 6 carbon atoms. Examples of $C_5$-$C_6$cycloalkyl include, cyclopentyl and cyclohexyl.

As used herein, except where explicitly stated otherwise, the term "heteroaryl" refers to a 5- or 6-membered monocyclic aromatic ring which comprises 1 or 2 heteroatoms independently selected from nitrogen and oxygen. Examples of heteroaryl include, furyl, pyrrolyl, imidazolyl, pyrazolyl, oxazolyl, isoxazolyl, pyrazinyl, pyridazinyl, pyrimidyl or pyridyl.

As used herein, the term "π-allylpalladium complex" refers to a palladium atom coordinated to an optionally substituted allyl group. Examples of π-allylpalladium complex include, but are not limited to, allylpalladium chloride, (2-Butenyl) chloropalladium (also known as crotylpalladium chloride), palladium (π-cinnamyl) chloride or (2-methylallyl)palladium chloride.

These π-allylpalladium complexes are typically provided in the form of a dimer, for example, allylpalladium chloride dimer, (2-Butenyl) chloropalladium dimer (also known as crotylpalladium chloride dimer), palladium (π-cinnamyl) chloride dimer or (2-methylallyl) palladium chloride dimer as shown below,

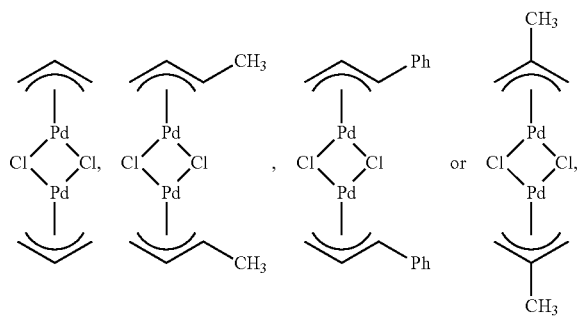

The π-allylpalladium complexes may also be provided with a phosphine ligand in a pre-formed complex as shown below,

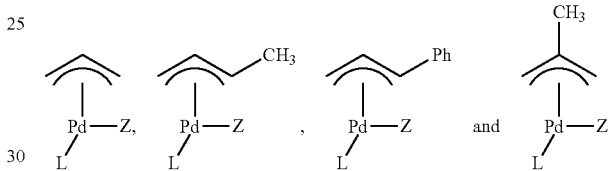

wherein L represents a phosphine ligand as defined herein, and Z is a coordinating anionic ligand, for example, Chlorine, Bromine, Iodine, trifluoroacetate or methanesulfonate.

In one embodiment of the invention each $R^1$ and $R^2$ are independently methyl or ethyl. More preferably $R^1$ and $R^2$ are both ethyl.

In an embodiment of the invention $R^3$ is $C_1$-$C_4$alkyl. Preferably $R^3$ is methyl or ethyl, more preferably $R^3$ is methyl.

In another embodiment of the invention X is Br or Cl, preferably X is Br.

In one embodiment of the invention the π-allylpalladium complex is selected from the group consisting of allylpalladium chloride, allylpalladium trifluoroacetate, (2-Butenyl) chloropalladium and (2-methylallyl)palladium chloride. Preferably, the π-allylpalladium complex is selected from the group consisting of allylpalladium chloride, allylpalladium trifluoroacetate and (2-Butenyl) chloropalladium. More preferably the π-allylpalladium complex is selected from the group consisting of allylpalladium chloride and (2-Butenyl) chloropalladium.

In one embodiment the π-allylpalladium complex is allylpalladium (II) chloride dimer.

In an embodiment of the invention the amount of π-allylpalladium complex is from 0.0001 to 30 mol % based on a compound of formula (II). Preferably the amount of π-allylpalladium complex is from 0.01 to 20 mol %, more preferably from 0.1 to 15 mol % and even more preferably from 1 to 10 mol % based on a compound of formula (II).

In another embodiment of the invention the molar ratio of π-allylpalladium complex to phosphine ligand or a salt thereof is from 1:1 to 1:6, preferably from 1:1 to 1:4

In a one embodiment of the invention the molar ratio of π-allylpalladium complex to phosphine ligand or a salt thereof is 1:1.

In another embodiment of the invention the molar ratio of π-allylpalladium complex to phosphine ligand or a salt thereof is 1:4.

In one embodiment of the invention the phosphine ligand is of the formula (IV)

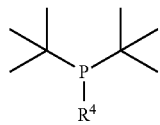

(IV)

or a suitable salt thereof,
wherein
$R^4$ is selected from the group consisting of $C_1$-$C_6$alkyl, $C_5$-$C_6$cycloalkyl, phenyl and heteroaryl, wherein the heteroaryl is a 5- or 6-membered aromatic ring which comprises 1 or 2 heteroatoms independently selected from N and O,
and wherein the phenyl or heteroaryl are optionally substituted by 1, 2, 3 or 4 $R^5$ substituents, which may be the same or different;
$R^5$ is selected from the group consisting of halogen, $C_1$-$C_4$alkyl, $C_1$-$C_4$alkoxy, N—$C_1$-$C_4$alkylamino, N,N-di$C_1$-$C_4$alkylamino and phenyl, wherein said phenyl is optionally substituted by 1, 2, 3 or 4 $R^6$ substituents, which may be the same or different;
$R^6$ is selected from the group consisting of $C_1$-$C_4$alkyl, $C_1$-$C_4$alkoxy, N—$C_1$-$C_4$alkylamino and N,N-di$C_1$-$C_4$alkylamino In a preferred embodiment of the invention the phosphine ligand is of the formula (IV)

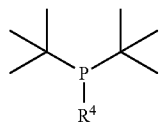

(IV)

or a suitable salt thereof,
wherein
$R^4$ is selected from the group consisting of $C_1$-$C_6$alkyl, phenyl and heteroaryl, wherein the heteroaryl is
a 5-membered aromatic ring which comprises 1 heteroatom independently selected from N and O, and wherein any of said phenyl or heteroaryl are optionally substituted by 1, 2, 3, 4 or 5 $R^5$ substituents, which may be the same or different;
$R^5$ is selected from the group consisting of $C_1$-$C_4$alkyl, $C_1$-$C_4$alkoxy, and phenyl, wherein the phenyl is optionally substituted by 1, 2, 3 or 4 $R^6$ substituents, which may be the same or different;
$R^6$ is selected from the group consisting of $C_1$-$C_4$alkyl, $C_1$-$C_4$alkoxy, N—$C_1$-$C_4$alkylamino and N,N-di$C_1$-$C_4$alkylamino.

In a more preferred embodiment of the invention the phosphine ligand or suitable salt thereof is selected from the group consisting of

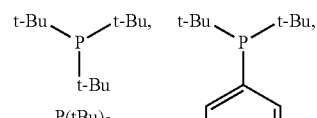

P(tBu)₃

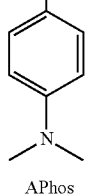

APhos

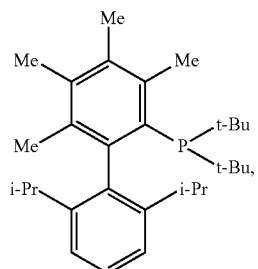

Me₄tBuXPhos

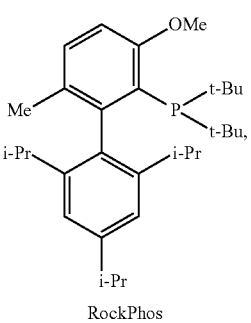

RockPhos

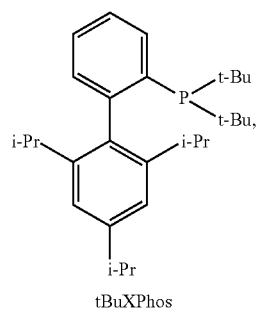

tBuXPhos

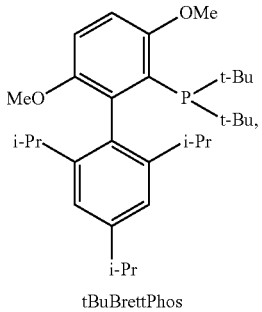

tBuBrettPhos

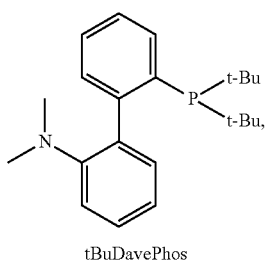

tBuDavePhos

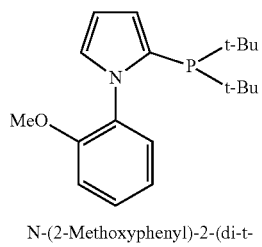

N-(2-Methoxyphenyl)-2-(di-t-butylphosphino)pyrrole

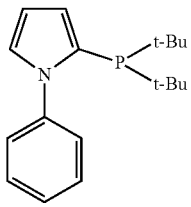

N-Phenyl-2-(di-t-butylphosphino)pyrrole and

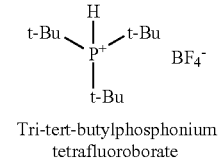

Tri-tert-butylphosphonium tetrafluoroborate

In a further more preferred embodiment of the invention the phosphine ligand or suitable salt thereof is selected from the group consisting of

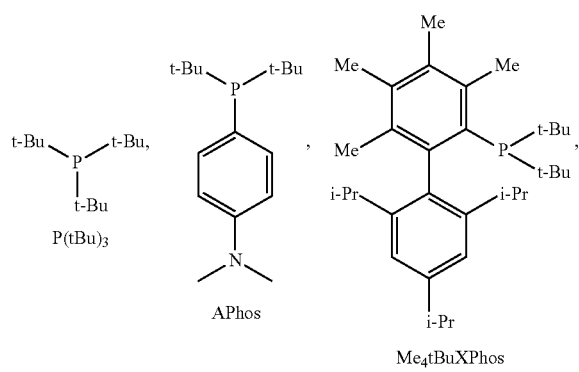

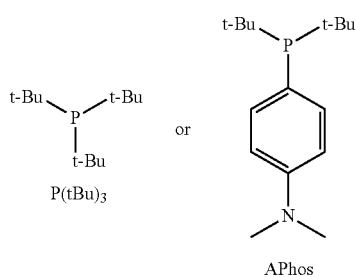 [SMILES: CC(C)(C)P(C(C)(C)C)C(C)(C)C ; CN(C)c1ccc(P(C(C)(C)C)C(C)(C)C)cc1 ; "P(tBu)3"]

In a yet even more preferred embodiment of the invention the phosphine ligand is

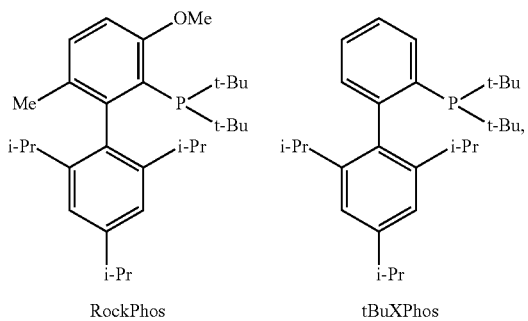

In a most preferred embodiment of the invention the phosphine ligand is

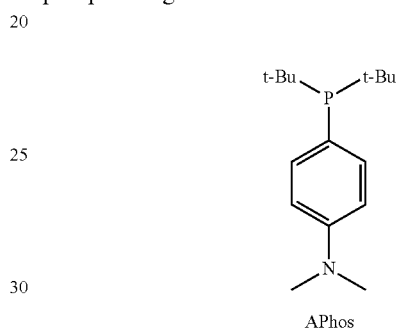

In one embodiment of the invention the π-allylpalladium complex and the phosphine ligand are separate before they are added to the reaction.

In another embodiment of the invention the π-allylpalladium complex is provided with a phosphine ligand as defined herein in a pre-formed complex. In this embodiment it should be understood that a further phosphine ligand as defined herein may optionally be present in the reaction in addition to the pre-formed complex.

In a further embodiment of the invention the pre-formed complex is of formula (Ib):

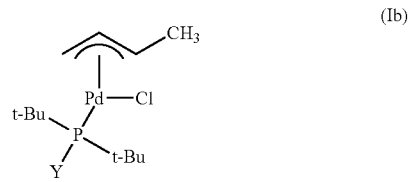 (Ib)

wherein

Y is selected from the group consisting of N,N-dimethylaniline and t-Bu.

In a more preferred embodiment of the invention the pre-formed complex is of formula (Ic):

In an even more further preferred embodiment of the invention the phosphine ligand or suitable salt thereof is selected from the group consisting of

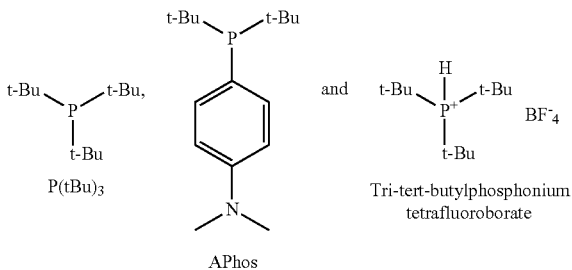

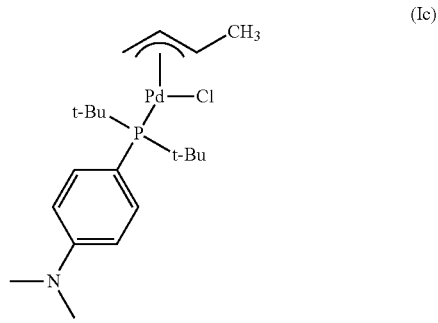

(Ic)

The process according to the invention is typically carried out in an organic solvent which are in principle all organic solvents that are inert under the reaction conditions.

Suitable organic solvents thus include, for example, 1,4-dioxane, toluene, N-methyl-2-pyrrolidone (NMP), dimethyl sulfoxide (DMSO), N,N-dimethylformamide (DMF), N,N-dimethylacetamide (DMAc), chlorobenzene, dichlorobenzene, Xylene, tetrahydrofuran, 2-methyltetrahydrofuran, methanol, ethanol, 1-propanol, 2-propanol, n-butanol, tert-butanol, polyethylene glycol (PEG), diethylene glycol dimethyl ether (diglyme), 2-methyl tert-butyl ether (MTBE) and cyclopentyl methy ether (CPME).

In a preferred embodiment of the invention the organic solvent is selected from the group consisting of 1,4-dioxane, toluene, N-methyl-2-pyrrolidone (NMP), Xylene, tetrahydrofuran, 2-methyltetrahydrofuran and tert-butanol. Preferably the organic solvent is 1,4-dioxane or toluene.

Suitable bases for the process according to the invention thus include, for example, organic bases such as triethylamine, diisopropylethylamine (DIPEA), pyridine, 1,4-diazabicyclo[2.2.2]octane (DABCO), 1,8-Diazabicyclo(5.4.0)undec-7-ene (DBU), sodium tert-butoxide, potassium tert-butoxide, lithium bis(trimethylsilyl)amide and sodium bis(trimethylsilyl)amide or inorganic bases such as LiOH, NaOH, KOH, Mg(OH)$_2$, Ca(OH)$_2$, NaNH$_2$, KNH$_2$, Li$_2$CO$_3$, Na$_2$CO$_3$, K$_2$CO$_3$, Cs$_2$CO$_3$, CaCO$_3$, MgCO$_3$, NaHCO$_3$, KHCO$_3$, Li$_3$PO$_4$, Na$_3$PO$_4$, K$_3$PO$_4$, Na$_2$HPO$_4$, K$_2$HPO$_4$, LiH$_2$PO$_4$, NaH$_2$PO$_4$ and KH$_2$PO$_4$.

The skilled person would appreciate that a preformed anion of a compound of formula (III), a compound of formula (III-a) below may also act as a base in the process of the invention.

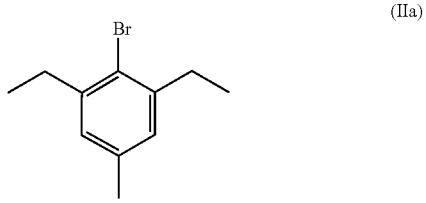

(III-a)

In one embodiment of the invention the base is selected from the group consisting of triethylamine, 1,8-Diazabicyclo(5.4.0)undec-7-ene (DBU), sodium tert-butoxide, potassium tert-butoxide, lithium bis(trimethylsilyl)amide, NaOH, KOH, Na$_2$CO$_3$, K$_2$CO$_3$, Cs$_2$CO$_3$, Na$_3$PO$_4$ and K$_3$PO$_4$. Preferably, the base is selected from the group consisting of potassium tert-butoxide, NaOH, KOH, Na$_2$CO$_3$, K$_2$CO$_3$, Cs$_2$CO$_3$, Na$_3$PO$_4$ and K$_3$PO$_4$. More preferably, the base is selected from the group consisting of potassium tert-butoxide, KOH, K$_2$CO$_3$ and K$_3$PO$_4$. Even more preferably, the base is KOH or K$_3$PO$_4$. Most preferably, the base is K$_3$PO$_4$.

The process of the present invention is preferably carried out under an inert atmosphere, such as nitrogen or argon.

The skilled person would appreciate that the temperature of the process according to the invention can vary depending on the choice of solvent used. Typically, the process according to the invention is carried out at a temperature from 40° C. to 120° C., preferably from 80° C. to 110° C.

The skilled person would also appreciate that the pressure of the process according to the invention can vary depending on the choice of solvent and temperature used. Typically, the process according to the invention is conducted at a pressure from 1 to 50 bar.

In a preferred embodiment of the invention there is provided a process for preparation of a compound of formula (Ia) (8-(2,6-diethyl-4-methyl-phenyl)-1,2,4,5-tetrahydropyrazolo[1,2-d][1,4,5]oxadiazepine-7,9-dione)

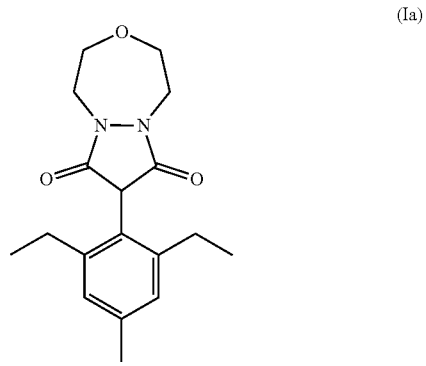 [SMILES: CCc1cc(C)cc(CC)c1C1C(=O)N2CCOCCN2C1=O]

(Ia)

said process comprising reacting a compound of formula (IIa)

(IIa)

with a compound of formula (III)

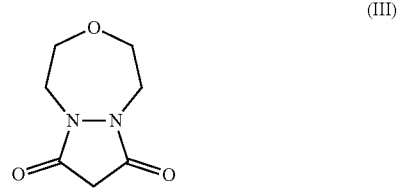 [SMILES: O=C1CC(=O)N2CCOCCN12]

(III)

the reaction being carried out
in an organic solvent, wherein the organic solvent is 1,4-dioxane or toluene;
in the presence of a π-allylpalladium complex, wherein the π-allylpalladium complex is selected from the group consisting of allylpalladium (II) chloride dimer, allylpalladium (II) trifluoroacetate dimer and (2-Butenyl) chloropalladium dimer;

and a phosphine ligand or salt thereof, selected from the group consisting of

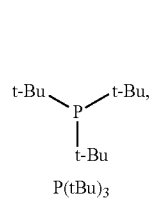 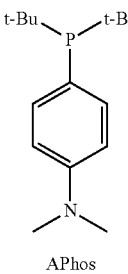 and 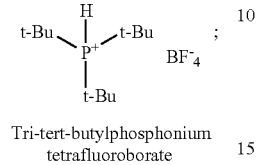

P(tBu)₃  APhos  Tri-tert-butylphosphonium tetrafluoroborate and
a base, wherein the base is K₃PO₄.

In another preferred embodiment of the invention there is provided a process for preparation of a compound of formula (Ia)

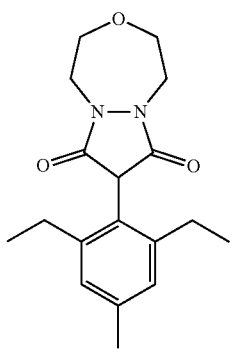

(Ia)

said process comprising reacting a compound of formula (IIa)

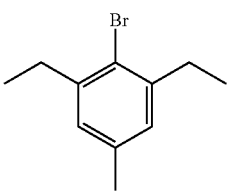

(IIa)

with a compound of formula (III)

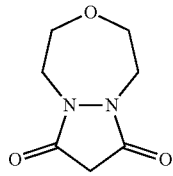

(III)

the reaction being carried out
in an organic solvent, wherein the organic solvent is 1,4-dioxane or toluene;
in the presence of a pre-formed complex of formula (Ic):

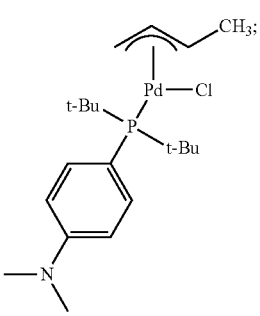

(Ic)

and a phosphine ligand or salt thereof, selected from the group consisting of

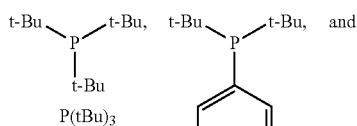

P(tBu)₃    APhos

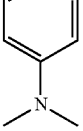

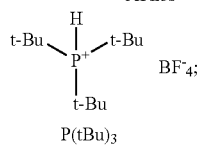

P(tBu)₃
Tri-tert-butylphosphonium tetrafluoroborate and
base, wherein the base is K₃PO₄.

There is further provided an intermediate compound of formula (III):

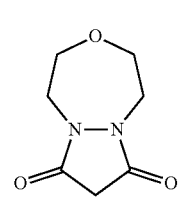

(III)

The compound of formula (III) according to the invention may be in free form, anionic (a compound of formula (III-a)) or in salt form.

The skilled person would appreciate that a compound of formula (Ia) can be converted into a compound of formula (Id) using known methods in the art, including but not limited to reaction of a compound of formula (Ia) with pivaloyl chloride and a suitable base, see for example Muehlebach et. al. Bioorg. Med. Chem. 17(2009) 4241-4256. This transformation is shown below:

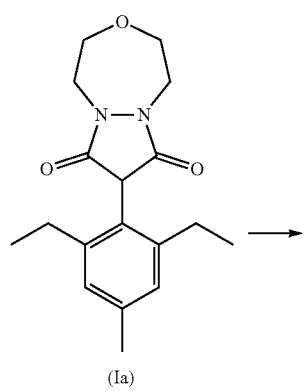

(Ia)

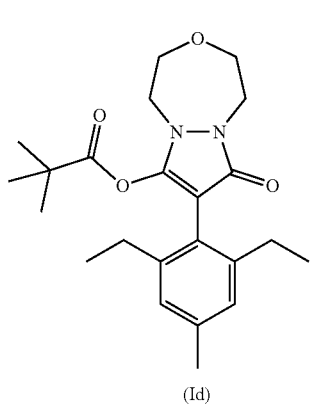

(Id)

In one embodiment there is provided a process according to the invention wherein a compound of formula (I) is further converted (for example by using pivaloyl chloride) to a compound of formula (Id) ([8-(2,6-diethyl-4-methyl-phenyl)-9-oxo-1,2,4,5-tetrahydropyrazolo[1,2-d][1,4,5]oxadiazepin-7-yl] 2,2-dimethylpropanoate, also known as pinoxaden).

Scheme 1 below describes the reactions of the invention in more detail.

Scheme 1 - Convergent synthesis of the compounds of formula (I) according to the invention.

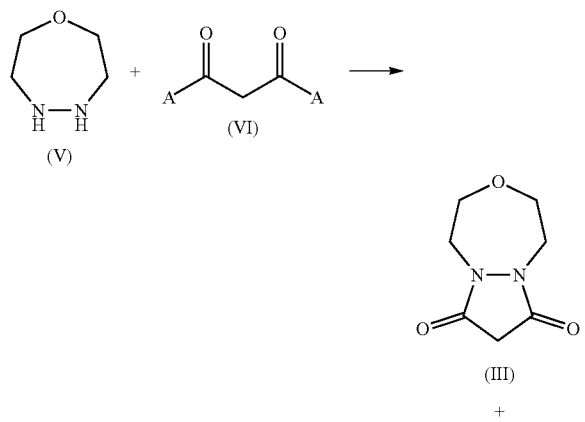

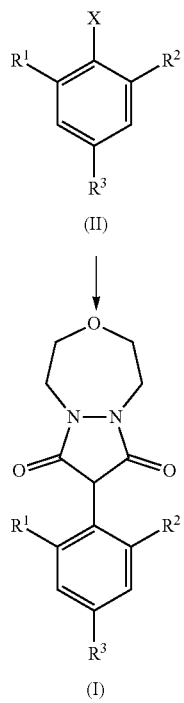

The compound of formula (III) may be made by the reaction of a compound of formula (V) or a salt thereof and a compound of formula (VI), wherein A is a suitable leaving group, for example -OMe, -OEt or Cl, in the presence of a base or an acid, and a suitable solvent. Suitable bases for this reaction include DIPEA and trimethylamine and suitable acids include para-toluenesulfonic acid (PTSA). Suitable solvents include, dichloromethane, chlorobenzene or xylene.

The compounds of formula (V) are known or can be prepared according to known methods, as described, for example, in WO 2006/045587. Compounds of formula (VI) are either known or are commercially available.

EXAMPLES

The following examples further illustrate, but do not limit, the invention. Those skilled in the art will promptly recognise appropriate variations from the procedures both as to reactants and as to reaction conditions and techniques.

The following abbreviations are used: s=singlet; br s=broad singlet; d=doublet; dd=double doublet; dt=double triplet; t=triplet, tt=triple triplet, q=quartet, quin=quintuplet, sept=septet; m=multiplet; GC=gas chromatography, RT=retention time, MH$^+$=molecular mass of the molecular cation, M=molar, Q$^1$HNMR=quantitative $^1$HNMR, HBTU=N,N,N',N'-Tetramethyl-O-(1H-benzotriazol-1-yl) uronium hexafluorophosphate, DIPEA=N,N-diisopropylethylamine, RT=room temperature.

$^1$H NMR spectra are recorded at 400 MHz unless indicated otherwise and chemical shifts are recorded in ppm.

Example 1

1,2,4,5-tetrahydropyrazolo[1,2-d][1, 4, 5]oxadiazepine-7,9-dione (Compound of formula III)

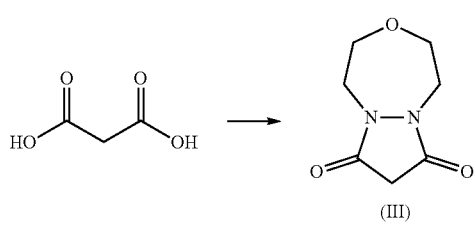

Procedure:

To a solution of malonic acid (0.39 g, 3.7 mmol, 98 mass %) in dichloromethane (12 mL) at room temperature was added portion wise HBTU (1.47 g, 3.8 mmol, 98 mass %). The solution was stirred for min at room temperature. To this solution 1,4,5-oxadiazepane (2 g, 2.9 mmol, 15 mass % in chlorobenzene) was added followed by dropwise addition of N,N-diisopropylethylamine (1.14 g, 8.64 mmol, 98 mass %) for 10 min at room temperature. The reaction mixture was stirred at room temperature for 3 h. After this time, the solvent was evaporated and product purified by column chromatography. Gradient: 2% MeOH in DCM Yield: 0.59 g (83%) as a White Solid, mp: 161-164° C.

¹H NMR (CDCl₃): δ 3.23 (s, 2H); 3.82 (t, J=4, 4H); 3.99 (t, J=4, 4H).

Example 2

8-(2,6-diethyl-4-methyl-phenyl)-1,2,4,5-tetrahydropyrazolo[1,2-d][1,4,5]oxadiazepine-7,9-dione

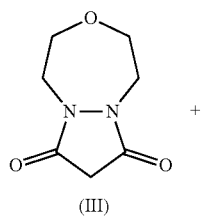

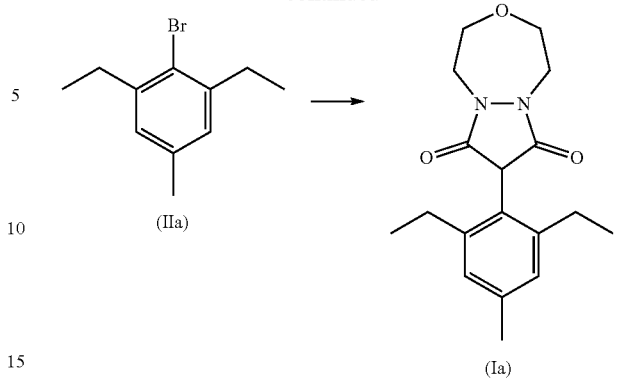

Procedure:

The reaction was conducted under a nitrogen atmosphere. To an empty oven-dried Schlenk tube (purged with N₂), was added 1,2,4,5-tetrahydropyrazolo[1,2-d][1,4,5]oxadiazepine-7,9-dione 0.468 g, 2.39 mmol, 87 mass %), potassium phosphate (0.953 g, 4.35 mmol, 97 mass %), 2-bromo-1,3-diethyl-5-methyl-benzene (0.5 g, 2.17 mmol, 97 mass %) and 1,4-dioxane (15 mL). This mixture was degassed with N₂ for 10 min. To this heterogeneous solution was added PdCl(crotyl) Aphos (0.051 g, 0.108 mmol, 98 mass %) and further degassed with N₂ for 10 min. The resulting solution was heated with stirring to reflux for 7 h. After this time, the tube was cooled, and the reaction mixture was acidified with 2M HCl. The mixture was extracted with DCM, organic fraction was dried with Na₂SO₄, filtered, concentrated and purified by washing with diethyl ether yielded a yellow solid. ¹H NMR (400 MHz, CDCl₃) σ 1.19 (t, J=7.6 Hz, 3H); 1.25 (t, J=7.6 Hz, 3H); 2.27 (q, J=7.6 Hz, 2H); 2.30 (s, 3H); 2.70 (q, J=7.6 Hz, 2H); 3.75-3.81 (m, 2H); 3.93-4.03 (m, 4H); 4.26-4.32 (m, 2H); 4.71 (s, 1H); 6.92 (s, 1H); 6.94 (s, 1H).

General Procedure:

A dry Schlenk flask equipped with a magnetic stir bar was charged with 1,2,4,5-tetrahydropyrazolo[1,2-d][1,4,5]oxadiazepine-7,9-dione (0.459 g; 2.348 mmol; 1.07 equiv), base (1.95 equiv) and dry solvent (15 mL). This mixture was evacuated and backfilled with nitrogen. This evacuation/nitrogen backfill cycle was repeated two additional times. To this heterogeneous solution was added the palladium catalyst (0.048 equiv) and 2-bromo-1,3-diethyl-5-methyl-benzene (0.500 g; 2.179 mmol; 1.0 equiv), further degassed with N₂ for 10 min. The resulting solution was heated with stirring to 105° C. for 7 h. After this time, the tube was cooled, and the reaction mixture was acidified to pH 2 with 2M HCl. The samples were then run on a GC to check conversion. The mixture was extracted with DCM, and organic extract dried over Na₂SO₄, filtered, concentrated and purified by wash with Diethyl ether.

The above general procedure was used to obtain the results referred to in Table 1 below.

TABLE 1

Summary of results for arylation of 1,2,4,5-tetrahydropyrazolo[1,2-d][1,4,5]oxadiazepine-7,9-dione with 2-bromo-1,3-diethyl-5-methyl-benzene

| Entry | Precursor | Catalyst Loading/ mol % | Added APhos Loading/ mol % | Base | Solvent | Product formed (GC area % or Q $^1$HNMR) |
|---|---|---|---|---|---|---|
| 1 | Pd(OAc)$_2$ | 5 | 10 | K$_3$PO$_4$ | 1,4-dioxane | N/D |
| 2 | [Pd(allyl)Cl]$_2$ | 5 | 10 | K$_3$PO$_4$ | 1,4-dioxane | 46% (Q iHNMR) |
| 3 | [Pd(2-Butenyl)Cl]$_2$ | 5 | 10 | K$_3$PO$_4$ | 1,4-dioxane | 54% (Q $^1$HNMR) |
| 4 | [Pd(cinnamyl)Cl]$_2$ | 5 | 10 | K$_3$PO$_4$ | 1,4-dioxane | 58% (GCarea %) |
| 5 | [Pd(2-methylallyl)Cl]$_2$ | 5 | 10 | K$_3$PO$_4$ | 1,4-dioxane | 53% (GCarea %) |
| 6 | [PdCl(crotyl)Aphos] | 5 | 0 | K$_3$PO$_4$ | 1,4-dioxane | 85% (Q $^1$HNMR) |
| 7 | [Pd(allyl)Cl]$_2$ | 5 | 10 | K$_2$CO$_3$ | 1,4-dioxane | 30% (GCarea %) |
| 8 | [Pd(allyl)Cl]$_2$ | 5 | 10 | KOH powder | 1,4-dioxane | 66% (GCarea %) |
| 9 | [Pd(allyl)Cl]$_2$ | 5 | 10 | K$_3$PO$_4$ | DEMBB | 21% (GCarea %) |
| 10[a] | [Pd(allyl)Cl]$_2$ | 5 | 10 | K$_3$PO$_4$ | 1,4-dioxane | 41% (GCarea %) |
| 11[b] | [Pd(allyl)Cl]$_2$ | 5 | 10 | K$_3$PO$_4$ | 1,4-dioxane | 16% (isolated) |

[a]2-chloro-1,3-diethyl-5-methy-benzene used as substrate instead of 2-bromo-1,3-diethyl-5-methyl-benzene
[b]P$^t$(Bu)$_3$ used as ligand.
N/D means not detected.

Example 3

General Procedure for Palladium Catalysed α-arylation

Into an oven-dried 35 mL carousel reaction tube fitted with a magnetic stirrer bar was added the palladium source, APhos (4-di-tert-butylphoshanyl-N,N-dimethyl-aniline, 0-20 mol %), 1,2,4,5-tetrahydropyrazolo[1,2-d][1,4,5]oxadiazepine-7,9-dione (1.2 equiv.) and K$_3$PO$_4$ (2.1 equiv.) under an atmosphere of N$_2$ gas. A solution of 2-bromo-1,3-diethyl-5-methyl-benzene (DEMBB, 1 equiv.) and mesitylene (0.25 equiv. as an internal standard) in 1,4-dioxane (1-3 ml) was purged of oxygen by bubbling with N$_2$ gas for 20 mins and then transferred to the reaction tube which was then placed immediately into the pre-heated carousel at 110° C. and stirred for 6 h.

Sampling procedure: A small aliquot of the reaction mixture was quenched with HCl (aq, 1 M) and extracted into EtOAc. The conversion was determined by NMR spectroscopy and/or GC analysis against mesitylene as an internal standard, or 1,3,5-trimethoxybenzene as an external standard.

The above general procedure (example 3) was used to obtain the results referred to in Table 2 below.

TABLE 2

Summary of results comparing differing palladium catalysts with the APhos ligand

| Entry | Precursor | Catalyst Loading/ mol % | Added APhos Loading/ mol % | [DEMBB]/ M | Total conversion of DEMBB/ % | Ratio, compound of formula (Ia) :ArH (selectivity %) |
|---|---|---|---|---|---|---|
| 1 | Pd(OAc)$_2$ | 5 | 10 | 0.13 | 4 | 0.2:1 (17) |
| 2 | Pd(OAc)$_2$ | 5 | 20 | 0.4 | 6 | 0.3:1 (25) |
| 3 | [Pd(allyl)Cl]$_2$ | 5 | 10 | 0.13 | 54 | 1.04:1 (51) |
| 4 | [Pd(allyl)Cl]$_2$ | 2.5 | 20 | 0.13 | 50 | 0.9:1 (47) |
| 5 | [Pd(allyl)Cl]$_2$ | 2.5 | 20 | 0.4 | 67 | 4:1 (80) |
| 6 | [PdCl(crotyl)Aphos] | 5 | 15 | 0.4 | 61 | 4:1 (80) |

[PdCl(crotyl) Aphos] is a pre-formed complex of formula (Ic) below:

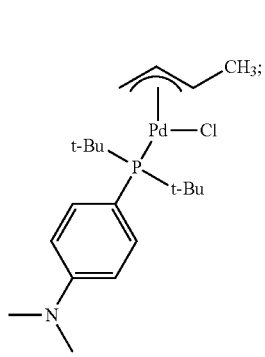

ArH is a compound of formula (IIb) below:

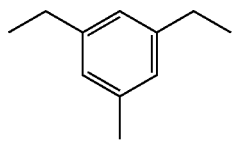

These results demonstrate that the allylpalladium (II) chloride dimer appears to be a more efficient catalyst than palladium (II) acetate. Palladium (II) acetate is not a competent catalyst precursor for the reaction with only a 4-6% conversion of DEMBB. The palladium catalyst pre-formed complex, [PdCl (crotyl) Aphos] also demonstrated good levels of conversion to the desired product.

What is claimed is:

1. A process for preparation of a compound of formula (I)

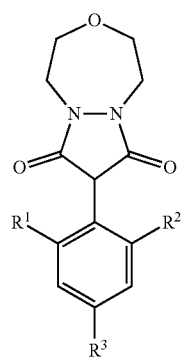

wherein
each $R^1$ and $R^2$ are independently $C_1$-$C_4$alkyl;
$R^3$ is selected from the group consisting of hydrogen and $C_1$-$C_4$alkyl;

said process comprising reacting a compound of formula (II)

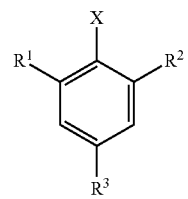

wherein
X is selected from the group consisting of Br, Cl, $CF_3SO_3$—, $CH_3C_6H_4SO_3$— and $CH_3SO_3$—, and $R^1$, $R^2$ and $R^3$ are as defined herein, with a compound of formula (III)

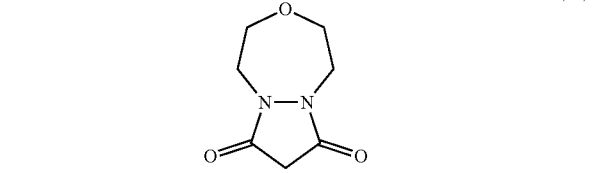

the reaction being carried out in the presence of a π-allylpalladium complex; and a phosphine ligand of the formula (IV)

or a suitable salt thereof,
wherein
$R^4$ is selected from the group consisting of $C_1$-$C_6$alkyl, $C_5$-$C_6$cycloalkyl, phenyl and heteroaryl,
wherein the heteroaryl is a 5- or 6-membered aromatic ring which comprises 1 or 2 heteroatoms independently selected from N and O,
and wherein the phenyl or heteroaryl are optionally substituted by 1, 2, 3, 4 or 5 $R^5$ substituents, which may be the same or different;
$R^5$ is selected from the group consisting of halogen, $C_1$-$C_4$alkyl, $C_1$-$C_4$alkoxy, N—$C_1$-$C_4$alkylamino, N,N-di$C_1$-$C_4$alkylamino and phenyl, wherein said phenyl is optionally substituted by 1, 2, 3 or 4 $R^6$ substituents, which may be the same or different;
$R^6$ is selected from the group consisting of $C_1$-$C_4$alkyl, $C_1$-$C_4$alkoxy, N—$C_1$-$C_4$alkylamino and N,N-di$C_1$-$C_4$alkylamino;
and a base.

2. A process according to claim 1, wherein X is Br.

3. A process according to claim 1, wherein each $R^1$ and $R^2$ are ethyl.

4. A process according to claim 1 wherein $R^3$ is methyl.

5. A process according to claim 1, wherein the π-allylpalladium complex is selected from the group consisting of allylpalladium chloride, allylpalladium trifluoroacetate, (2-Butenyl) chloropalladium, palladium (π-cinnamyl) chloride and (2-methylallyl)palladium chloride.

6. A process according to claim 1, wherein the π-allylpalladium complex is allylpalladium chloride or (2-Butenyl)chloropalladium.

7. A process according to claim 1, wherein the π-allylpalladium complex is present in the amount of from 1 to 10 mol % based on the compound of formula (II).

8. A process according claim 1 wherein the molar ratio of π-allylpalladium complex to phosphine ligand or phosphine ligand salt is 1:4.

9. A process according to claim 1, wherein the π-allylpalladium complex is provided with a phosphine ligand as defined herein in a pre-formed complex.

10. A process according to claim 1, wherein the phosphine ligand of formula (IV) is 4-di-tert-butylphosphanyl-N,N-dimethyl-aniline.

11. A process according to claim 1, wherein the organic solvent is 1,4-dioxane or toluene.

12. A process according to claim 1, wherein the base is K$_3$PO$_4$.

13. A process according to claim 1, wherein the reaction of a compound of formula (II) with a compound of formula (III) is at a temperature of from 80° C. to 110° C.

14. A compound of formula (III):

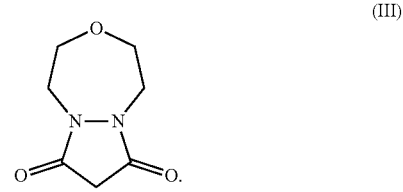 [SMILES: O=C1CC(=O)N2CCOCCN12]

(III)

15. A process according to claim 1, wherein a compound of formula (I) is further converted to pinoxaden.

* * * * *